(12) United States Patent
Petersen et al.

(10) Patent No.: US 7,671,243 B2
(45) Date of Patent: Mar. 2, 2010

(54) METHOD AND DEVICE FOR USING REACTION HEAT DURING THE PRODUCTION OF 1,2-DICHLOROETHANE

(75) Inventors: Sven Petersen, Kelkheim (DE); Michael Benje, Darmstadt (DE); Peter Kammerhofer, Burgkirchen (DE)

(73) Assignees: Uhde GmbH, Dortmund (DE); Vinnolit GmbH & Co. KG, Burgkirchen (DE)

( * ) Notice: Subject to any disclaimer, the term of this patent is extended or adjusted under 35 U.S.C. 154(b) by 0 days.

(21) Appl. No.: 11/922,617

(22) PCT Filed: Jun. 27, 2006

(86) PCT No.: PCT/EP2006/006163
§ 371 (c)(1), (2), (4) Date: Aug. 12, 2009

(87) PCT Pub. No.: WO2007/000304
PCT Pub. Date: Jan. 4, 2007

(65) Prior Publication Data
US 2009/0306439 A1    Dec. 10, 2009

(30) Foreign Application Priority Data
Jun. 28, 2005 (DE) .................. 10 2005 030 511
Jun. 28, 2005 (DE) .................. 10 2005 030 512
Sep. 15, 2005 (DE) .................. 10 2005 044 177

(51) Int. Cl.
  *C07C 17/02* (2006.01)
(52) U.S. Cl. ........................................ 570/246
(58) Field of Classification Search .................. 570/246
  See application file for complete search history.

(56) References Cited

U.S. PATENT DOCUMENTS 4,834,847 A * 5/1989 McIntyre .................. 205/461

* cited by examiner

*Primary Examiner*—Jafar Parsa
(74) *Attorney, Agent, or Firm*—Marshall & Melhorn, LLC

(57) ABSTRACT

The invention relates to a method for using reaction heat produced by reaction during the production of 1,2-dichloroethane from ethylene and chlorine in a direct chlorination reactor. The chlorine is produced in a sodium chloride electrolysis and the reaction heat, during the formation of 1,2-dichloroethane is used at least partially for the evaporation of NaOH, which is produced during NaCl-electrolysis for producing the required chlorine for direct chlorination, as a coupling product. The invention also relates to a device for carrying out said method, comprising a multi-tube heat exchanger comprising two fixed tubular plates and a NaOH-liquid phase part, and the caustic soda passes through the inside of the tube and 1,2-dichloroethane passes the outside of the tube. The heat exchanger also comprises devices for feeding and distributing the caustic soda in the inside of the tube.

7 Claims, 6 Drawing Sheets

METHOD AND DEVICE FOR USING REACTION HEAT DURING THE PRODUCTION OF 1,2-DICHLOROETHANE

BACKGROUND OF THE INVENTION

The invention relates to a method and an apparatus for utilizing the heat of reaction evolved in the preparation of 1,2-dichloroethane, hereinafter referred to as EDC. EDC serves predominantly as intermediate in the preparation of monomeric vinyl chloride, hereinafter referred to as VCM, from which polyvinyl chloride, PVC, is finally prepared. The conversion of EDC into VCM forms hydrogen chloride HCl. EDC is therefore preferably prepared from ethene $C_2H_4$ and chlorine $Cl_2$ in such a way that a balance is achieved between the hydrogen chloride HCl produced and consumed in the reactions according to the following reaction equations:

$$Cl_2 + C_2H_4 \rightarrow C_2H_4Cl_2 \text{ (pure EDC)} + 218 \text{ kJ/Mol} \quad (1)$$

$$C_2H_4Cl_2 \text{ (dissociation EDC)} \rightarrow C_2H_3Cl \text{ (VCM)} + HCl - 71 \text{ kJ/Mol} \quad (2)$$

$$C_2H_4 + 2 HCl + \tfrac{1}{2}O_2 \rightarrow C_2H_4Cl_2 \text{ (crude EDC)} + H_2O + 238 \text{ kJ/Mol} \quad (3)$$

The process for preparing VCM having an HCl balance, hereinafter referred to as "balanced VCM process" for short, comprises:

a direct chlorination in which a part of the EDC required is produced from ethene $C_2H_4$ and chlorine $Cl_2$ and is passed on as pure EDC; the utilization of the heat of reaction produced in this direct chlorination is a central aspect of the invention;

an oxychlorination in which the other part of the EDC is produced from ethene $C_2H_4$, hydrogen chloride HCl and oxygen $O_2$ and is passed on as crude EDC;

a fractionating EDC purification in which the crude EDC together with the recycle EDC recirculated from the VCM fractionation is freed of the by-products formed in the oxychlorination and in the EDC pyrolysis in order to obtain a feed EDC suitable for use in the EDC pyrolysis; the utilization of the heat of reaction of the direct chlorination in the EDC purification is a central aspect of the invention;

an EDC pyrolysis in which the pure EDC is combined with the feed EDC and in which the mixture then known as dissociation EDC is thermally dissociated; the dissociation gas obtained contains VCM, hydrogen chloride HCl and unreacted EDC and also by-products;

a VCM fractionation in which the pure VCM desired as product is separated off from the dissociation gas and the other significant dissociation gas constituents hydrogen chloride HCl and unreacted EDC are separately recovered as materials of value and are recirculated as reusable feed in the form of recycle HCl or recycle EDC in the balanced VCM process.

Plants which serve for the preparation of pure EDC and do not operate according to the balanced VCM process are usually designed as pure direct chlorinations which operate only according to equation (1). The invention likewise relates to plants which are designed according to the balanced VCM process and also to those which have only a direct chlorination, and to mixed forms of the two types.

The chlorine $Cl_2$ required in the direct chlorination is usually produced from sodium chloride NaCl in an electrolysis plant. Sodium hydroxide NaOH having a concentration of about 33% is formed here as coproduct. Owing to the high toxicity of the chlorine $Cl_2$ produced, efforts are made to avoid transport over long distances if possible. For this reason, a plant for the direct chlorination of ethylene $C_2H_4$ in which the chlorine $Cl_2$ is directly processed further is usually located in the immediate vicinity of a plant for preparing sodium hydroxide NaOH and chlorine $Cl_2$.

The plant for the direct chlorination of ethylene does not have to be present in an integrated facility but can produce EDC in "stand-alone operation", with the relatively nonhazardous "transport form" of the chlorine being transported to other sites in order to be processed into VCM there. The EDC prepared by the process described, for example, in WO 01/34542 A2, in particular, is so pure that it does not require further work-up by distillation. For this reason, when such a plant is operated in the "stand-alone mode", there is no longer the opportunity of recovering heat by means of column heating of EDC distillation columns, for example those which were present in the integrated facility for the "balanced VCM process" which is made up of direct chlorination, oxychlorination and EDC dissociation.

In this set-up, the considerable heat of reaction therefore has to be removed by means of large amounts of cooling water and/or air coolers, but each of these are undesirable for economic reasons. It is therefore an object of the invention to pass the heat evolved in the direct chlorination to a use and to achieve a significant reduction in the cooling water requirement.

If the direct chlorination is used within a balanced VCM process, it has to be taken into account that the secondary components formed in the dissociation gas in the EDC pyrolysis reduce the product purity of the VCM. The purification of the VCM by removal of the secondary components is accordingly complicated. A dissociation EDC which has been largely freed of impurities is therefore used in the EDC pyrolysis. For the large number of techniques by means of which the corresponding and disadvantageous by-products and/or secondary components can be avoided or, if appropriate, removed, reference may again be made to the document WO 01/34542 A2, in particular the prior art acknowledged there. It was able to be shown here that the heat of reaction liberated in the direct chlorination process by reaction of ethene $C_2H_4$ and chlorine $Cl_2$ to form liquid EDC is sufficient to operate the purification columns for EDC produced in the balanced VCM process.

However, a disadvantage of the process presented there is that the utilization of the heat present in the EDC can take place only at relatively high temperatures, i.e. predominantly above about 100° C. Although the operation of the apparatuses for purifying the EDC can be achieved by means of the evolved heat alone, the further cooling of the EDC produced, e.g. for later use, still has to be carried out by means of cooling water, for which large amounts of cooling water are still required.

A further disadvantage of the process presented there is that the heat of reaction used for heating the purification columns requires the removal of a corresponding quantity of heat of condensation of the vapour. This removal is, according to the conventional state of the art, usually likewise achieved by means of cooling water which has to be provided in large quantities.

BRIEF SUMMARY OF THE INVENTION

It is therefore a further object of the invention to achieve further optimization of the utilization of the evolved heat of the balanced VCM process, in particular the direct chlorination, and to achieve a significant reduction in the total cooling water requirement.

The invention achieves this object by utilizing at least part of the heat of reaction from the formation of 1,2-dichloroethane in the direct chlorination reactor for the evaporation of NaOH produced as coproduct in the NaCl electrolysis for the preparation of the chlorine required for the direct chlorination.

Especially in remote regions, transport costs for transporting away the sodium hydroxide NaOH produced in the NaCl electrolysis play an important role. These transport costs can be reduced significantly if the sodium hydroxide solution produced at a concentration of about 33% is evaporated to 50%. Such a plant for the evaporation of sodium hydroxide NaOH can be operated, for example, under reduced pressure at an absolute pressure of 133 mbar and a temperature of 60° C. The evaporation can naturally also be carried out from concentrations other than 33% to concentrations other than 50%, depending on what is desired by the consumer and on the quantity of heat evolved.

The heat of reaction which is liberated in the direct chlorination can be used in various ways for the evaporation of the sodium hydroxide. The following embodiments of the method can be combined readily and allow great flexibility in the matching of the heat utilization to existing plants and also in the case of newly designed plants.

In an embodiment of the invention, at least part of the heat of condensation of the EDC vapour taken off from the direct chlorination is used for evaporation of the sodium hydroxide produced. Such an embodiment is advantageous especially when a direct chlorination in "stand-alone operation" is used or if the purification by distillation of the EDC produced in the balanced VCM process cannot take up the entire heat of reaction made available in this way. In this case, EDC vapour from the top of the direction chlorination reactor is used to heat, by means of its heat of condensation, the outside of evaporator tubes which can be configured as falling film evaporator tubes and in which sodium hydroxide is evaporated. The condensate composed of pure EDC can also serve to evaporate the sodium hydroxide with further cooling in a further heat exchanger, for example a plug-in tube exchanger.

In a further embodiment of the invention, the sensible heat of a liquid EDC recycle stream taken off from the reactor is likewise used for evaporating sodium hydroxide. When this is combined with other streams which remove heat of reaction, care has to be taken to ensure that catalyst-containing EDC which is to be recirculated to the reactor circuit of the direct chlorination reactor is not mixed with pure EDC which is to be discharged from the process as product.

In a further embodiment of the invention, the EDC produced, which is taken off in gaseous or liquid form from the reactor for the direct chlorination, is firstly utilized for the indirect heating of purification columns and only after the EDC has transferred part of its heat energy thereat a relatively high temperature is it passed on for further transfer of energy in the sodium hydroxide evaporation where it transfers heat energy at a lower temperature to sodium hydroxide in indirect heat exchange. If a balanced VCM process is used for preparing EDC and VCM, the purification columns required for this purpose can preferably be heated before the remaining heat of reaction is utilized for the evaporation of sodium hydroxide.

Further embodiments of the invention make use of the fact that the same heat of reaction which is introduced in the indirect heating of purification columns has to be removed again in the subsequent condensation of the vapour from these same purification columns, so that it only so-to-say passes through the purification column and is in the process thermodynamically devalued. However, a considerable part of this heat of reaction passing through the column can, despite a reduced temperature, likewise still be used for sodium hydroxide evaporation.

Thus, in a further embodiment of the invention, the EDC-containing vapour from a distillation column for removing components which have a boiling point higher than that of EDC are used for the evaporation of sodium hydroxide. Such a distillation column is, as high boiler column, a customary part of the balanced VCM process. It is not to be mistaken for the vacuum column which follows the high boiler column and whose temperature at the top would not be sufficiently high for the use according to the invention.

In a further embodiment of the invention, the water-containing vapour from a distillation column for removing water and components having a boiling point lower than that of 1,2-dichloroethane is likewise used for the evaporation of sodium hydroxide. Such a distillation column is, as low boiler column, a customary part of the balanced VCM process.

Processes in which the EDC produced in the direct chlorination is taken off in vapour form and is from there introduced directly into a distillation are also known; a direct chlorination of this type is described, for example, in U.S. Pat. No. 4,873,384. The direct chlorination reactor in this case simultaneously forms the bottom boiler of the subsequent purification column or integrates this into the bottom of the purification column itself. The heat of this reaction in this way passes through the adjoining distillation column and is obtained for removal in the condensation of the vapour. In one embodiment of the invention, at least part of the heat of condensation of the vapour obtained in the purification by distillation of EDC produced from ethene and chlorine in a direct chlorination reactor is used for the evaporation of the sodium hydroxide produced.

Further embodiments of the invention concern the apparatuses used for transferring the heat energy of the EDC to the sodium hydroxide NaOH to be evaporated. Use is here made mainly of an upright shell-and-tube heat exchanger, preferably a falling film evaporator, having two fixed tube plates and an NaOH bottom part in which the sodium hydroxide NaOH is conveyed in the inside of the tubes from the top downward and the heat transfer medium, i.e. EDC or vapour from distillation columns, is conveyed around the outside of the tubes.

If gaseous EDC or vapour from distillation columns is used in the sodium hydroxide evaporation, the heat transfer in the shell-and-tube apparatus takes place in cocurrent. The EDC vapour introduced at the top of the shell-and-tube apparatus condenses during passage through the apparatus and can be taken off in liquid form at the bottom.

If liquid EDC is used in the sodium hydroxide evaporation, the heat transfer can be effected either in the shell-and-tube apparatus, but then advantageously in countercurrent, or by means of a plugged-in bundle of heat exchanger tubes in the sodium hydroxide liquid or by means of a heat exchanger which is located outside the sodium hydroxide liquid and is operated in the circulation mode, e.g. of the kettle type.

All the above-described methods can also be employed additively or in combination. If the above shell-and-tube apparatus is to be operated both with EDC vapour and with liquid EDC, the shell-and-tube apparatus can be divided horizontally. Of course, it has to be ensured that the individual vapour streams from different distillation columns are not able to become mixed with one another.

The sodium hydroxide evaporation is usually carried out in multistage evaporation plants which comprise, for example, a plurality of evaporation apparatuses connected in series. The measures according to the invention described here can therefore also be applied separately to different stages or evaporation apparatuses of such a plant. Thus, for example, one stage can be heated by means of gaseous EDC while another stage is heated by means of liquid EDC. However, the measures according to the invention can also be used only at one stage or simultaneously at a plurality of stages of a multistage plant for the evaporation of sodium hydroxide. It is also possible to operate various stages at different reduced pressures in order to permit different temperatures of the individual heat transfer media.

BRIEF DESCRIPTION OF THE DRAWINGS

The invention is illustrated below with the aid of 8 drawings, but the method of the invention is not restricted to these specific cases.

DETAILED DESCRIPTION OF THE INVENTION

Figure 1:
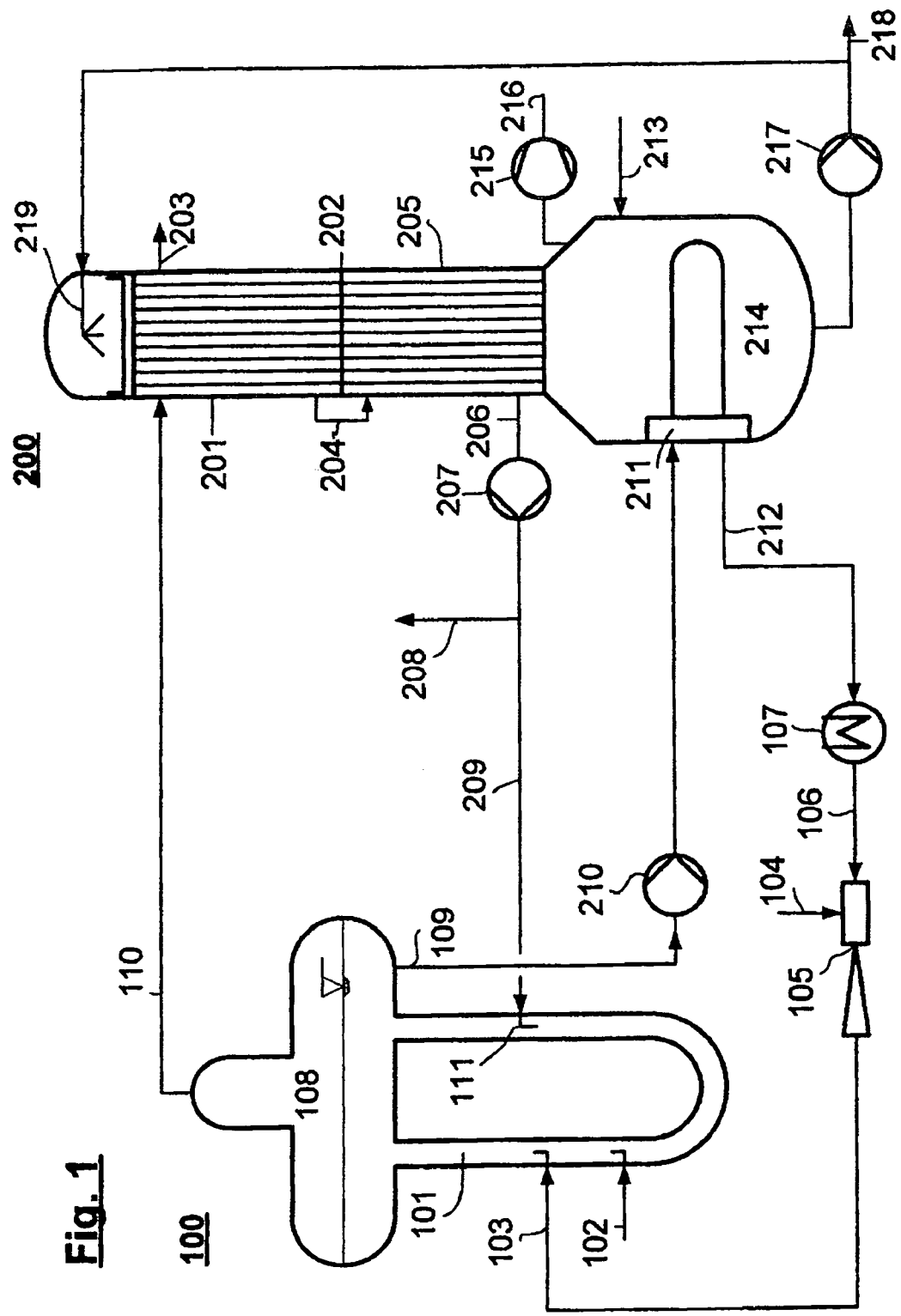
FIG. 1 shows a possible arrangement with a direct chlorination reactor and a sodium hydroxide evaporation corresponding to method claims 2 and 3.

FIG. 1 shows a combination of a sodium hydroxide evaporation with a direct chlorination reactor which produces EDC in "stand-alone operation" and whose heat of reaction heats the sodium hydroxide evaporation both in accordance with method claim 2 by means of gaseous EDC and in accordance with method claim 3 by means of liquid EDC.

The direct chlorination 100 comprises a loop 101 filled with liquid, an introduction of ethylene 102, an addition of chlorine dissolved in EDC 103, with the chlorine gas 104 having been dissolved beforehand, in the injector 105, in liquid EDC 106 which had been cooled beforehand to a low temperature in the EDC cooler 107 to improve the solubility, also a outgassing vessel 108, an offtake facility for liquid EDC 109, and offtake facility for gaseous EDC 110 and a feed point for recycle EDC 111, with the respective feed points and offtake facilities also being able to be present in multiple form for practical reasons. In the loop 101 filled with liquid, chlorine and ethylene react with one another to form boiling EDC which vaporizes in the outgassing vessel 108 together with unreacted starting materials and inert accompanying gas.

Gaseous EDC 110 is introduced into the upper jacket space 201 of the shell-and-tube heat exchanger 202, shown here as being divided horizontally, of the sodium hydroxide evaporation 200 where it condenses and thereby releases heat, but is not significantly undercooled in order to avoid pressure fluctuations of the EDC vapour. Incondensable constituents are discharged via the inert gas offtake 203. Here, it has to be ensured by means of suitable technical measures that an explosive gas mixture cannot be formed in the jacket space of the shell-and-tube heat exchanger. Such measures are known to those skilled in the art and are not subject matter of the invention. The EDC condensate 204 is drained into the lower jacket space 205 of the horizontally divided shell-and-tube heat exchanger 202 where the liquid EDC is cooled. The draining of the condensed EDC into the lower jacket space can optionally be assisted by means of a pump (not shown).

The cooled pure EDC 206 is taken off from the horizontally divided shell-and-tube heat exchanger 202 by the condensate pump 207 and is divided into two substreams: product EDC 208 and recycle EDC 209. The product EDC 208 is, after cooling in a product cooler (not shown) conveyed to the battery limits, and the recycle EDC 209 is fed back into the reactor.

The catalyst-containing EDC taken off from the offtake facility for liquid EDC 109 is conveyed by means of the EDC pump 210 into the plug-in cooler 211 which is installed in the bottom part 214 of the sodium hydroxide evaporation 200 and is cooled there. The cooled EDC 212 from the plug-in cooler 211 is cooled further in the circulation cooler 107 and fed to the injector nozzle 105 where it acts as driving stream to suck in and dissolve chlorine 104. The stream 103 of chlorine dissolved in EDC is then fed to the direct chlorination reactor 100.

33% strength sodium hydroxide solution 213 is fed into the bottom part 214 of the sodium hydroxide evaporation 200 and evaporated under reduced pressure. The pressure is maintained by the vacuum pump 215 which discharges the liberated water vapour 216. The sodium hydroxide pump 217 discharges part of the sodium hydroxide solution which has been concentrated to about 50% as product NaOH 218 and conveys another part to the sodium hydroxide distributor 219 which distributes the sodium hydroxide solution to be concentrated into the interior of the tubes of the shell-and-tube heat exchanger 202. The vaporization energy for the evaporation is introduced here by the heat of condensation and/or the sensible heat of the condensed EDC.

The following numerical example based on a simulation calculation for a plant having an annular capacity of 250 000 tonnes of EDC serves as an illustration. In a plant of this size, the reaction enthalpy is about 19.1 MW (218 kJ/mol of EDC). An annual capacity of 250 000 tonnes of EDC corresponds to an amount of chlorine of 22.5 tonnes of chlorine/h, which in turn corresponds to a sodium hydroxide production of about 25.4 tonnes/h (calculated as 100% NaOH). The sodium hydroxide is obtained at a concentration of 33% at a temperature of about 80° C. and is concentrated to 50% by vacuum evaporation. This corresponds to an amount of water to be vaporized of about 26.2 tonnes/h or a heating power of 14.6 MW.

This heat requirement can be covered completely by the heat evolved in the direct chlorination; thus, about 76% of the heat of reaction is recoverable in this application, which is an advantage of the invention. The evaporation is operated at a reduced pressure of about 133 mbar absolute and a temperature of 60° C. The remaining heat of reaction to be removed is removed by means of heat exchangers in the direct chlorination plant.

Figure 2:
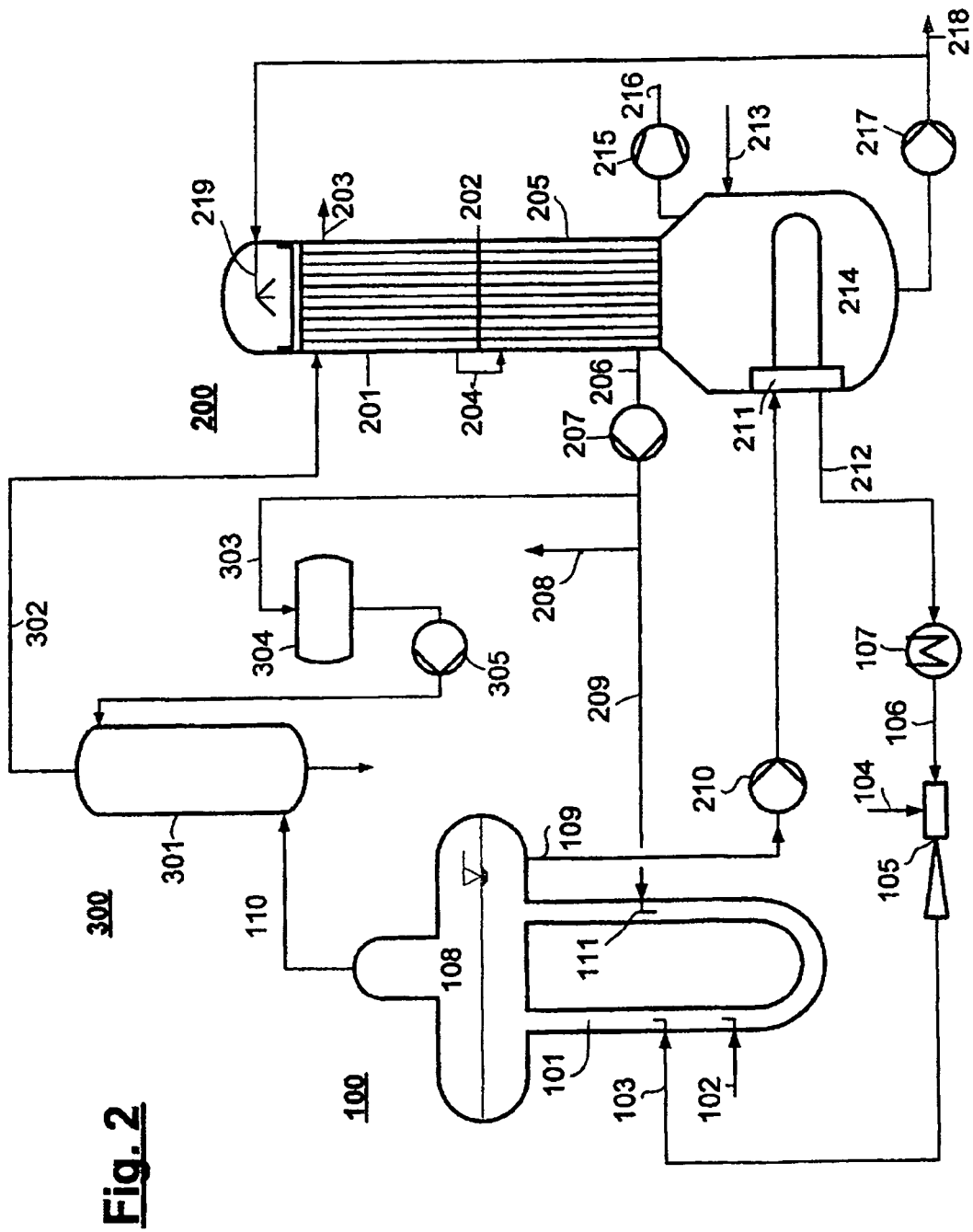
FIG. 2 shows a possible arrangement with a direct chlorination reactor having a connected purification column and a sodium hydroxide evaporation corresponding to method claim 4, FIG. 3 and FIG. 4 each show a possible combination of a sodium hydroxide evaporation with a direct chlorination reactor and heat recovery according to the balanced VCM process, based on the teachings of WO 01/34542 A2 and corresponding to method claim 5.

FIG. 2 shows a direct chlorination reactor with connected distillation 300 for the purification of the EDC produced. The make-up of the apparatus groups direct chlorination 100 and sodium hydroxide evaporation 200 is the same as that described in FIG. 1. In contrast to the mode of operation described in FIG. 1, the EDC vapour which is taken from the direct chlorination reactor is firstly purified by distillation in the purification column 301. The vapour 302 from the purification column 301 is introduced into the upper jacket space 201 of the sodium hydroxide evaporation 200. The sodium hydroxide evaporation 200 serves as vapour condenser of the purification column 301. The vapour condensate 303 is conveyed by the condensate pump 207 into the top reservoir 304 of the purification column 301 and from there is fed by means of the reservoir pump 305 to the top of the purification column 301.

Figure 3:
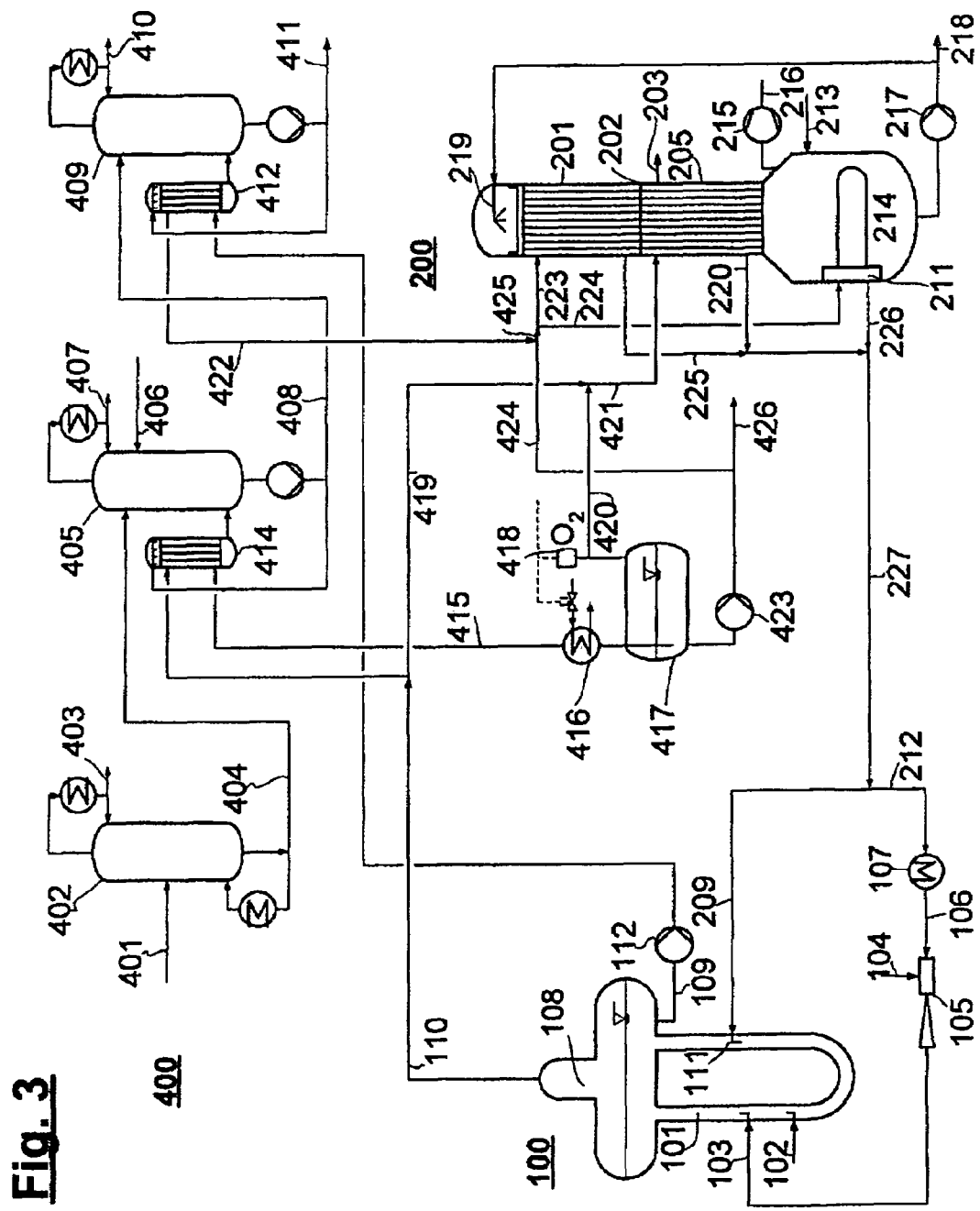
Figure 4:
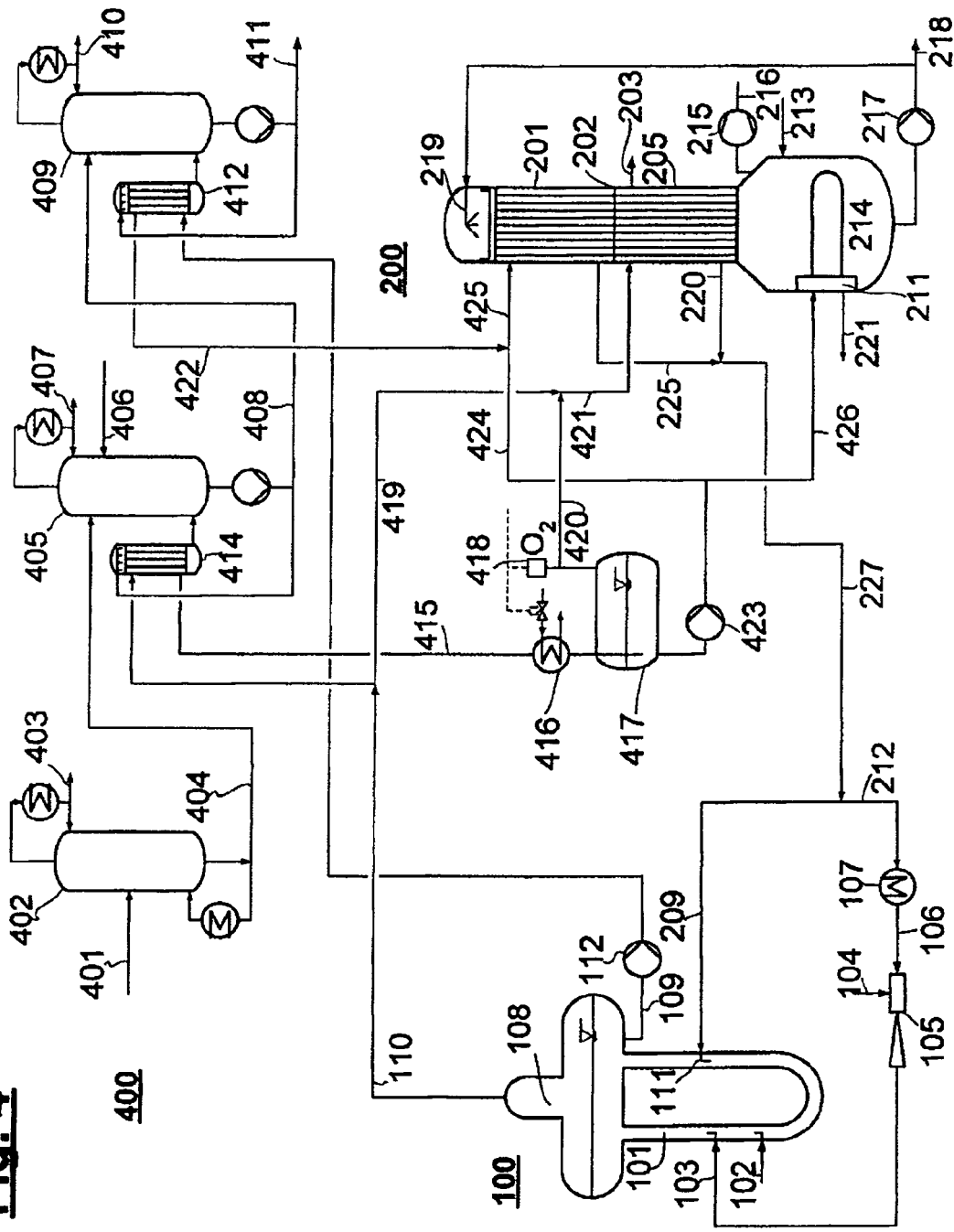

FIG. 3 and FIG. 4 show how the EDC from the oxychlorination and the unreacted EDC from the EDC pyrolysis are purified in an energy-intensive EDC distillation in the EDC purification 400 of the balanced VCM process. The crude EDC 401 from the oxychlorination, which is not shown here, is firstly freed of water and low boilers in a low boiler column 402 and the water and low boilers are discharged via the low boiler line 403. The EDC obtained as bottom product from the low boiler column, which still contains high boilers, is then fed via the EDC line 404 to the high boiler column 405. The unreacted EDC from the EDC pyrolysis likewise contains high boilers and is fed via the EDC line 406 to the high boiler column 405.

In the high boiler column 405, the streams fed in are fractionated. Purified EDC is taken off at the top of the high boiler column 405 via the vapour line 407 and is obtained as pure EDC. The high boilers accumulate in the bottom of the high boiler column 405. The bottom stream 408 from the high boiler column 405 is worked up in the vacuum column 409. At the top of the vacuum column 409, pure EDC is taken off via the EDC vapour line 410. The bottom output 411 from the vacuum column 409 comprises high boilers and a small residual proportion of EDC.

The heating of the columns 405 and 409 is effected as follows: liquid EDC 109 is taken off from the direct chlorination reactor 100 and is fed and discharged as heating medium into/from the falling film evaporator 412 of the vacuum column 409. EDC vapour 413 is branched off from gaseous EDC 110 from the direction chlorination 100 and fed as heating medium to the falling film evaporator 414 of the high boiler column 405. In the falling film evaporators 412 and 414, the liquid to be heated flows down from the top of the evaporator body as a uniformly distributed, boiling film on the inside of the heating tubes under the force of gravity and is partly vaporized. The major part of the EDC vapour condenses on the outside of the falling film evaporator 414. Of course, other heat exchangers, e.g. normal thermosiphon reboilers, can also be used.

The upward stream 415 from the falling film evaporator 414 can be fed to an optional trim condenser 416 which serves to regulate this system. Liquid EDC is subsequently separated from incondensable components in the receiver 417. Here, it has to be ensured by means of suitable measures that an explosive mixture of oxygen, residual ethene and EDC vapour cannot be formed during the condensation. For this reason, an oxygen measuring instrument 418, for example, measures the oxygen content and an associated regulator regulates the inflow of cooling medium to the trim condenser 416 correspondingly, but further regulators can also be connected to the trim condenser 416. If a regulating facility is not necessary, the trim condenser 416 can also be omitted. The formation of an explosive gas mixture can also be prevented by means of other measures which are not subject matter of the invention.

Depending on the particular requirement of the high boiler column 405, a surplus of EDC vapour can be present for at least part of the time. In this case, an EDC substream 419 is branched off from the gaseous EDC 110 and combined with incondensable components 420 from the receiver 417. This combined EDC vapour stream 421 serves to heat the lower section 205 of the shell-and-tube apparatus of the sodium hydroxide evaporation 200, with the EDC being condensed and taken off as EDC condensate 220. The incondensable components are taken off as offgas 221 and subjected to a further treatment which is not shown here.

A liquid EDC stream 109 is taken off from the outgassing vessel 108 by means of the circulation pump 112 and fed to the falling film evaporator 412 for heating the vacuum column 409. The EDC stream 422 which has been cooled slightly after outward transfer of sensible heat is combined with part of the pure EDC 424 taken off from the receiver 417 by means of the pump 423 to form the pure EDC 425 and fed to the sodium hydroxide evaporation 200. The other part of the pure EDC 424 taken off from the receiver 417 by means of the pump 423 serves as product EDC 426.

FIG. 3 shows a way of obtaining product EDC at a higher temperature. A person skilled in the art will choose this method if he wishes to process the product EDC directly in the next process step to produce VCM because he can then save part of the reheating. Here, product EDC 426 is used without further utilization of the heat contained in it. However, if EDC is to be conveyed into large, unpressurized storage tanks, the procedure shown in FIG. 4 can be utilized: there, the product EDC 426 is cooled to below 70° C. in the plug-in cooler 211 which is located in the bottom part 214 of the sodium hydroxide evaporation 200 and is from there conveyed as cooled product EDC 222 to storage. As an alternative, it would be possible to locate the EDC cooler in the pump sodium hydroxide circuit.

FIG. 3 and FIG. 4 show how liquid EDC can be used in the sodium hydroxide evaporation 200. In FIG. 3, the EDC stream 425 is branched off and one part 223 of it is fed into the upper section 201 of the shell-and-tube apparatus of the sodium hydroxide evaporation 200 and the other part 224 is fed into a plug-in heat exchanger 211 which serves as bottom heating. The EDC streams 225 and 226 which have been cooled to about 65-70° C. are combined with the EDC condensate 220 and form the recycle stream 227. In FIG. 4, the EDC stream 425 is not divided but is instead fed directly into the upper section 201 of the shell-and-tube apparatus of the sodium hydroxide evaporation 200. As an alternative, an arrangement in the pump circuit of the sodium hydroxide would also be possible. The EDC stream 225 which has been cooled to about 70° C. is combined with the EDC condensate 220 and these together form the recycle stream 227.

The recycle stream 227 is divided into the EDC substreams 209 and 212. The further process shown in FIGS. 3 and 4 corresponds in terms of the sodium hydroxide evaporation and the direct chlorination to that which has already been described for FIG. 1.

The following numerical example based on a simulation calculation serves to illustrate the process variants depicted in FIGS. 3 and 4: the calculation is carried out for a plant having an annual capacity of 250 000 tonnes of EDC. In a plant of this size, the reaction enthalpy is about 19.1 MW (218 kJ/mol of EDC). Of this, it is possible to recover:

| | |
|---|---|
| By column heating using EDC vapour: | 7900 kW |
| By column heating using liquid EDC: | 2050 kW |
| By feed preheating using liquid EDC: | 1310 kW |
| Total: | 11260 kW |

These add up to about 60% of the total heat of reaction.

An annual capacity of 250 000 tonnes of EDC corresponds to a chlorine requirement of 22.5 tonnes/h, which in turn corresponds to a sodium hydroxide production (calculated as 100% NaOH) of about 25.4 tonnes/h. The sodium hydroxide is obtained at a concentration of 33% at a temperature of about 80° C. and is concentrated to 50% by vacuum evaporation. This corresponds to an amount of water to be vaporized of about 26.2 tonnes/h or a heating power of 14.6 MW. Of this, about 4.2 MW can be additionally recovered by cooling the recycle EDC stream from 100° C. to 70° C. in a sodium hydroxide evaporator. This improves the degree of utilization of the heat of reaction from 60% to 80%. The remaining heat of reaction to be removed is removed by means of heat exchangers in the direct chlorination plant.

Figure 5:
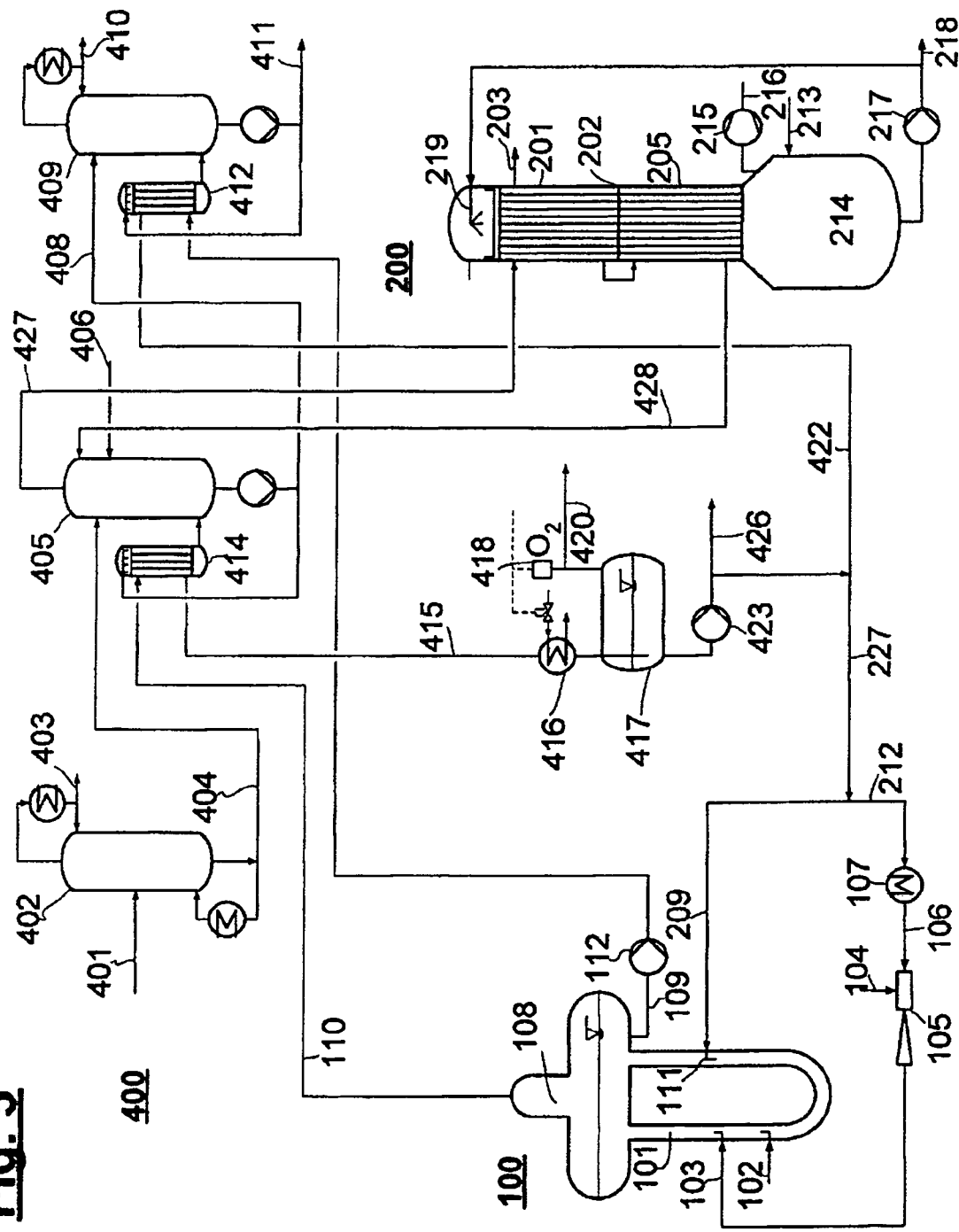
FIG. 5 shows a possible arrangement with a direct chlorination reactor, purification columns with vapour condensation and a sodium hydroxide evaporation corresponding to method claims 6 and 7.

FIG. 5 shows, like FIGS. 3 and 4, the balanced VCM process in which the heat of reaction from the direct chlorination 100 is used for heating purification columns. Regardless of how the further utilization of the heat in the EDC streams leaving the boilers is effected, i.e. for instance in the manner of the invention as shown in FIGS. 3 and 4 or in another way, the vapour from the high boiler column 405 can also be utilized for the sodium hydroxide evaporation. For this purpose, the high boiler vapour 427 is fed not into a conventional condenser but into the upper section 201 of the shell-and-tube apparatus of the sodium hydroxide evaporation 200 and the EDC condensate taken off from the sodium hydroxide evaporation is recirculated as runback 428 to the high boiler column 405 and fed there to the top of the column.

The high boiler vapour 427 is pure EDC which can be dealt with in a manner analogous to the gaseous EDC 110 as shown in FIG. 1 or in a manner analogous to the EDC vapour 303 as shown in FIG. 2, for which reference may be made to the respective descriptions. Since this stream is pure EDC, it can also be mixed with other EDC vapours or EDC condensates in the process which have a similar purity. The processes depicted in FIGS. 3, 4 and 5 can therefore readily be combined with one another.

The following numerical example based on a simulation calculation serves as an illustration: the calculation is carried out for a plant having an annual capacity of 400 000 tonnes of EDC. In a plant of this size, about 16.2 MW of thermal power can be recovered in the high boiler column at a pressure at the top of 1.11 bar and a temperature of about 87° C., by means of which about 44 tonnes/h of sodium hydroxide (calculated as 100% NaOH) can be concentrated from 33 to 50 percent by weight.

Figure 6:
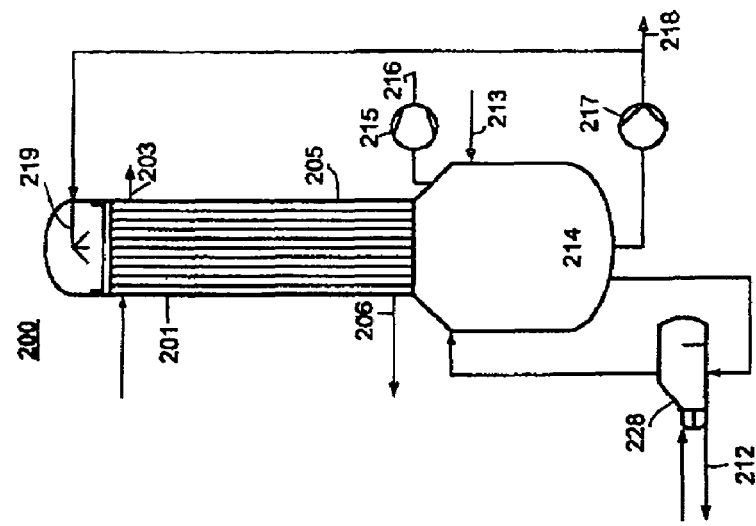
FIG. 6 to 8 show illustrative embodiments of the apparatus for the sodium hydroxide evaporation corresponding to the apparatus claims.
Figure 7:
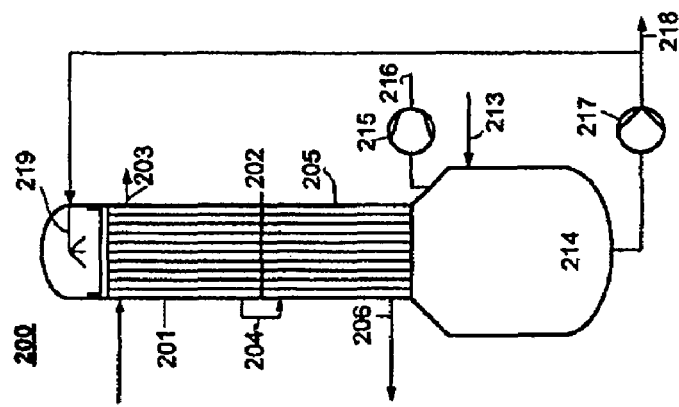
Figure 8:
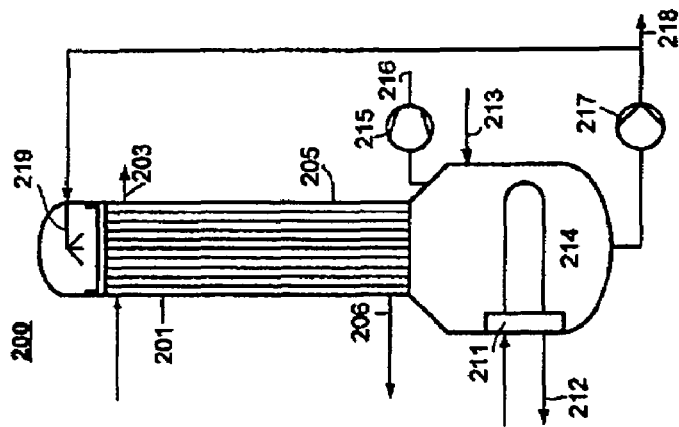

FIG. 6 to 8 show illustrative embodiments of the apparatus. FIG. 6 shows a falling film evaporator without a horizontal division, comprising a shell-and-tube heat exchanger which has 2 fixed tube plates and an NaOH bottom part and is configured so that sodium hydroxide solution is to be conveyed in the insides of the tubes and 1,2-dichloroethane is to be conveyed on the outside of the tubes and also has facilities for introducing and distributing sodium hydroxide solution into the interior of the tubes and facilities which make it possible to condense 1,2-dichloroethane on the outside of the tubes and also allow the introduction of gaseous 1,2-dichloroethane and the discharge of inert gas and of 1,2-dichloroethane condensate.

FIG. 7 additionally shows a shell-and-tube apparatus having facilities which make it possible to introduce liquid 1,2-dichloroethane and also to discharge it, with a divided shell-and-tube apparatus being used.

FIG. 8 shows an external circulation vaporizer of the kettle type 228 for operation using liquid 1,2-dichloroethane as heating medium for the bottom part of the shell-and-tube heat exchanger. This embodiment can be advantageously employed when a plurality of liquid EDC streams which either have different purities or of which one contains a catalyst for operation of the direct chlorination reactor are used and must not be mixed with one another.

LIST OF REFERENCE NUMERALS USED

100 Direct chlorination
101 Loop filled with liquid
102 Ethylene feed
103 Dissolved chlorine
104 Chlorine gas
105 Injector
106 Liquid EDC
107 EDC cooler
108 Outgassing vessel
109 Liquid EDC
110 Gaseous EDC
111 Recycle EDC
112 Circulation pump
200 Sodium hydroxide evaporation
201 Upper jacket space
202 Shell-and-tube heat exchanger
203 Inert gas offtake
204 EDC condensate
205 Lower jacket space
206 Pure EDC
207 Condensate pump
208 Product EDC
209 Recycle EDC
210 EDC pump
211 Plug-in cooler
212 EDC
213 33% strength sodium hydroxide solution
214 Bottom part
215 Vacuum pump
216 Water vapour
217 Sodium hydroxide pump
218 Product NaOH
219 Sodium hydroxide distributor
220 EDC condensate
221 Offgas
222 Cooled product EDC
223 Part
224 Part
225 EDC stream
226 EDC stream
227 Recycle stream
228 Kettle-type circulation vaporizer
300 Distillation
301 Purification column
302 Vapour
303 Vapour condensate
304 Top reservoir
305 Reservoir pump
400 EDC purification
401 Crude EDC
402 Low boiler column
403 Low boiler line
404 EDC line
405 High boiler column
406 EDC line
407 Vapour line
408 Bottom stream
409 Vacuum column
410 EDC vapour line
411 Bottom offtake
412 Falling film evaporator
413 EDC vapour 414 Falling film evaporator
415 Output stream
416 Trim condenser
417 Receiver
418 Oxygen measuring instrument
419 EDC substream
420 Incondensable components
421 EDC vapour stream
422 EDC stream
423 Pump
424 Pure EDC
425 Pure EDC
426 Product EDC
427 High boiler vapour
428 Runback

The invention claimed is:

1. A method of utilizing the heat of reaction in the preparation of 1,2-dichloroethane from ethene and chlorine in a direct chlorination reactor, with the chlorine being produced in a sodium chloride electrolysis, wherein at least part of the heat of reaction from the formation of 1,2-dichloroethane in the direct chlorination reactor is utilized for the evaporation of NaOH produced as coproduct in the NaCl electrolysis for the preparation of the chlorine required for the direct chlorination.

2. The method according to claim 1, wherein at least part of the heat of condensation of the 1,2-dichloroethane vapor taken off from the direct chlorination is used for evaporation of the sodium hydroxide produced.

3. The method according to claim 1, wherein at least part of the sensible heat of the liquid 1,2-dichloroethane taken off from the direct chlorination is used for evaporation of the sodium hydroxide produced.

4. The method according to claim 1, wherein at least part of the heat of condensation of the vapor obtained in the purification by distillation of 1,2-dichloroethane produced from ethene and chlorine in a direct chlorination reactor is used for evaporation of the sodium hydroxide produced.

5. The method according to claim 1, wherein the 1,2-dichloroethane produced, which is taken off in gaseous or liquid form from the reactor for the direct chlorination, is firstly utilized for the indirect heating of purification columns and only after the EDC has transferred part of its heat energy there at a relatively high temperature is it passed on for further transfer of energy in the sodium hydroxide evaporation where it transfers heat energy at a lower temperature to sodium hydroxide in indirect heat exchange.

6. The method according to claim 5, wherein at least part of the heat of condensation of the vapor from a distillation whose boiler is operated using heat of reaction generated in the direct chlorination reaction of ethene and chlorine is used for evaporation of the sodium hydroxide produced.

7. The method according to claim 5, wherein the 1,2-dichloroethane-containing vapor from a distillation column for removing components which have a boiling point higher than that of 1,2-dichloroethane are used for the evaporation of sodium hydroxide.

* * * * *